(12) United States Patent
Wu et al.

(10) Patent No.: US 11,957,817 B2
(45) Date of Patent: Apr. 16, 2024

(54) METHOD FOR DEGRADING ORGANISM

(71) Applicant: NATIONAL TSING HUA UNIVERSITY, Hsinchu (TW)

(72) Inventors: Jyh-Ming Wu, Hsinchu (TW); Srinivaas Masimukku, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 887 days.

(21) Appl. No.: 16/924,181

(22) Filed: Jul. 9, 2020

(65) Prior Publication Data

US 2020/0338226 A1 Oct. 29, 2020

Related U.S. Application Data

(62) Division of application No. 15/835,474, filed on Dec. 8, 2017, now abandoned.

(51) Int. Cl.
*A61L 9/16* (2006.01)
*A61L 9/012* (2006.01)
(Continued)

(52) U.S. Cl.
CPC ............. *A61L 9/16* (2013.01); *A61L 9/012* (2013.01); *C02F 1/34* (2013.01); *C02F 1/725* (2013.01); *H10N 30/092* (2023.02); *H10N 30/852* (2023.02); *C02F 1/36* (2013.01); *C02F 2101/30* (2013.01); *C02F 2101/308* (2013.01);
(Continued)

(58) Field of Classification Search
None
See application file for complete search history.

(56) References Cited

U.S. PATENT DOCUMENTS

| 6,217,741 B1 * | 4/2001 | Doi ........................ A61L 2/035 205/742 |
| 2010/0247390 A1 * | 9/2010 | Tanaka ..................... C02F 1/36 422/186 |

(Continued)

FOREIGN PATENT DOCUMENTS

CN 106178008 A * 12/2016 ............... A61L 2/02

OTHER PUBLICATIONS

Document entitled an Ultrasound-piezoelectric Cooperative Sterilization Technology, machine translation of CN 106178008 A provided by Clarivate (Year: 2016).*

(Continued)

*Primary Examiner* — Holly Kipouros
(74) *Attorney, Agent, or Firm* — CKC & Partners Co., LLC

(57) ABSTRACT

A method for degrading an organism includes steps as follows. A composite structure is provided, wherein the composite structure includes a degradation activity donor and a supporter. The degradation activity donor has a piezoelectric property. The supporter carries the degradation activity donor, wherein the degradation activity donor is completely or partially covered by the supporter. A contacting step is conducted, wherein the composite structure is contacted with a medium. The medium includes at least one organism and water. A degrading step is conducted, wherein a mechanical perturbation is generated in the medium to polarize the degradation activity donor, and a separation of an electron-hole pair is generated for degrading the organism.

8 Claims, 14 Drawing Sheets
(1 of 14 Drawing Sheet(s) Filed in Color)

(51) Int. Cl.
    *C02F 1/34*            (2023.01)
    *C02F 1/36*            (2023.01)
    *C02F 1/72*            (2023.01)
    *C02F 101/30*        (2006.01)
    *C02F 101/32*        (2006.01)
    *C02F 103/30*        (2006.01)
    *H10N 30/092*       (2023.01)
    *H10N 30/85*        (2023.01)

(52) U.S. Cl.
    CPC .... *C02F 2101/322* (2013.01); *C02F 2103/30* (2013.01); *C02F 2303/04* (2013.01); *C02F 2305/023* (2013.01)

(56) References Cited

U.S. PATENT DOCUMENTS

| | | | |
|---|---|---|---|
| 2013/0026108 A1* | 1/2013 | Yager | C02F 1/46114 210/748.04 |
| 2015/0182652 A1* | 7/2015 | Baik | B01J 31/0237 427/535 |
| 2019/0078239 A1* | 3/2019 | Ando | H10N 30/857 |

OTHER PUBLICATIONS

Metals Handbook, Ed. Davis, 1998, ASM International, p. 118 (Year: 1998).*
Composite Materials and Material Engineering II, Ed. Zhu, 2018, Trans Tech Publications, p. 210 (Year: 2018).*
Lin et al., Single- and few-layers MoS2 nanocomposite as piezo-catalyst in dark and self-powered active sensor, available online Dec. 8, 2016, Nano Energy 31, pp. 575-581 (Year: 2016).*
Li, The Investigation of ZnO/ Poly(vinylidene) Fluoride Nanocomposites for Orthopedic Applications with Improved Mechanical, Piezoelectric, and Antimicrobial Properties, Aug. 21, 2017, Northeastern University (Year: 2017).*
Bacteriological Analytical Manual, 5th Edition, Aug. 1978, Food and Drug Administration, p. A-56 (Year: 1978).*
Plastics Handbook, 5th Edition, 2019, Hanser Publishers, Table 7.12 (Year: 2019).*
Li et al., ZnO—Zn/CNT hybrid film as light-free nanocatalyst for degradation reaction, 2013, Nano Energy, vol. 2 Issue 6, pp. 1329-1336 (Year: 2013).*
Wu et al., Piezoelectricity of single-atomic-layer MoS2 for energy conversion and piezotronics, 2014, Nature, vol. 514 (Year: 2014).*

* cited by examiner

METHOD FOR DEGRADING ORGANISM

RELATED APPLICATIONS

The present application is a Divisional Application of the U.S. application Ser. No. 15/835,474, filed Dec. 8, 2017, the entire content of which is hereby incorporated herein by reference.

BACKGROUND

Technical Field

The present disclosure relates to a composite structure, a method for manufacturing the same, a method for degrading an organic material using the same, and a method for sterilizing using the same. More particularly, the present disclosure relates to a composite structure which can provide a degradation activity, a method for manufacturing the same, a method for degrading an organic material using the same, and a method for sterilizing using the same.

Description of Related Art

Conventionally, organic pollutants are often degraded with a photocatalyst. The photocatalyst is a substance which can accelerate a chemical reaction after irradiated with light. The common photocatalysts include gallium phosphide (GaP), gallium arsenide (GaAs), cadmium sulfide (CdS), stannic oxide ($SnO_2$), zinc oxide (ZnO), titanium dioxide ($TiO_2$), and so on.

The photocatalyst can generate a separation of electron-hole pairs after irradiated with light, in which the holes have oxidation ability and the electrons have reduction ability. The holes and the electrons can react with water molecules and oxygen molecules on a surface of the photocatalyst so as to generate reactive free radicals, such as hydroxyl radicals (OH·) and superoxide ions ($O_2^-$). The hydroxyl radicals have strong oxidation ability, the superoxide ions have strong reduction ability. By redox reactions, the photocatalyst can spoil cell membranes so as to achieve the sterilizing effect or can degrade organic gases or organic materials into water and carbon dioxide. Accordingly, a deodorization effect and a water purification effect can be achieved. The reaction between the holes and the water molecules and the reaction between the electrons and the oxygen molecules can be illustrated by Equation (1), Equation (2) and Equation (3):

$$h_{VB}^+ + H_2O \rightarrow H^+ + OH·  \quad (1);$$

$$h_{VB}^+ + OH^- \rightarrow OH·  \quad (2); \text{ and}$$

$$e_{CB}^- + O_2 \rightarrow O_2^-  \quad (3).$$

However, the catalytic activity of the photocatalyst is induced only when a certain energy is provided. Take the titanium dioxide for example, an energy greater than 3.2 eV (electronvolt) is required to induce the catalytic activity thereof, which is equivalent to an UV light with a wavelength lower than 387.5 nm. Although the sun light includes the UV light with the wavelength lower than 387.5 nm, the ratio of the UV light in the sun light is low. Therefore, the sun light cannot completely induce the catalytic activity of the titanium dioxide.

For solving the foregoing problem, a product equipped with an UV lamp is provided, whereby the photocatalyst is directly irradiated with the UV light for effectively enhancing the catalytic activity thereof. However, the UV light with a shorter wavelength is harmful to human body, so only can be used under certain conditions or environments, which is quite limited in use. Moreover, replacing the sun light with the UV lamp, an extra energy consumption is increased, which does not meet the demands of environmental protection and increases the cost.

Nano powders with a degradation activity which can be induced by an external force but not by the irradiation of light are developed. However, when the nano powders are applied to degrade the organic pollutants in wastewater. It is difficult to recover the nano powders by centrifugal method due to excessive light weights thereof, which causes a second pollution. Moreover, structural damages of the nano powders can be caused by the external force. The nano powders tend to be broken after used. Accordingly, it is unfavorably to use the nano powders repeatedly.

To sum up, how to develop a new degradation material, which does not rely on the irradiation of light with short wavelength and can provide desired degradation activity, tends not to cause the second pollution, and can be used repeatedly, is the goal of the related academia and industries.

SUMMARY

According to one aspect of the present disclosure, a method for degrading an organism includes steps as follows. A composite structure is provided, wherein the composite structure includes a degradation activity donor and a supporter. The degradation activity donor has a piezoelectric property. The supporter carries the degradation activity donor, wherein the degradation activity donor is completely or partially covered by the supporter. A contacting step is conducted, wherein the composite structure is contacted with a medium. The medium includes at least one organism and water. A degrading step is conducted, wherein a mechanical perturbation is generated in the medium to polarize the degradation activity donor, and a separation of an electron-hole pair is generated for degrading the organism.

BRIEF DESCRIPTION OF THE DRAWINGS

The patent or application file contains at least one drawing executed in color. Copies of this patent or patent application publication with color drawing(s) will be provided by Office upon request and payment of the necessary fee. The present disclosure can be more fully understood by reading the following detailed description of the embodiments, with reference made to the accompanying drawings as follows.

DETAILED DESCRIPTION

Composite Structure

Figure 1:
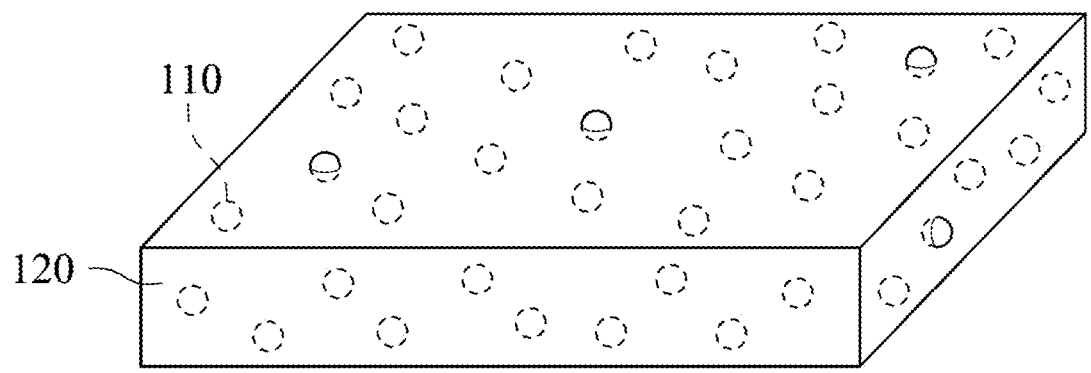
FIG. 1 is a three-dimensional (3D) view of a composite structure according to the 1st embodiment of the present disclosure.

FIG. 1 is a 3D view of a composite structure 100 according to the 1st embodiment of the present disclosure. In FIG. 1, the composite structure 100 includes a degradation activity donor 110 and a supporter 120. The degradation activity donor 110 has a piezoelectric property. The supporter 120 carries the degradation activity donor 110, wherein the degradation activity donor 110 is completely or partially covered by the supporter 120. The degradation activity donor 110 can provide a piezo-catalyst effect and does not rely on the irradiation of light with short wavelength to induce the degradation activity thereof, which is favorable for reducing the energy consumption. Moreover, with the degradation activity donor 110 is carried by the supporter 120, the difficulty of recovering the degradation activity donor 110 by centrifugal method due to an excessive light weight thereof can be eased, which can prevent a second pollution. Moreover, the degradation activity donor 110 can be protected by the supporter 120, the damage degree of the degradation activity donor 110 caused by an external force can be reduced, which is favorable for repeated use.

The term "piezoelectric property" refers to an ability of a substance to generate an electric charge when a mechanical stress is applied, or to generate a mechanical deformation when an electric field is applied.

The term "piezo-catalyst effect" refers that the separation of electron-hole pairs of the degradation activity donor 110 induced by the mechanical stress can cause the generation of the reactive free radicals, such as hydroxyl radicals and superoxide ions, so as to provide the degradation activity for degrading organic materials or spoiling cell membranes.

The degradation activity donor 110 can be a ferroelectric material, a pyroelectric material, a two-dimensional material with a non-centrosymmetric structure or a combination thereof. The phrase "the degradation activity donor 110 can be a ferroelectric material, a pyroelectric material, a two-dimensional material with a non-centrosymmetric structure or a combination thereof" refers that the degradation activity donor 110 can be one of the ferroelectric material, the pyroelectric material or the two-dimensional material with the non-centrosymmetric structure; alternatively, the degradation activity donor 110 can be a mixture formed by mixing at least two of the ferroelectric material, the pyroelectric material and the two-dimensional material with the non-centrosymmetric structure in any ratio. For example, the degradation activity donor 110 can be but is not limited to $NaKC_4H_4O_6 \cdot 4H_2O$, $BaTiO_3$, $KH_2PO_4$, $CaTiO_3$ or $LiTaO_3$. For further example, the two-dimensional material with the non-centrosymmetric structure can be but is not limited to $MoS_2$, $WTe_2$, $MoSe_2$, $WS_2$ or a combination thereof. When the degradation activity donor 110 is the two-dimensional material with the non-centrosymmetric structure, the degradation activity donor 110 has a single-layer structure or a few-layer structure. Moreover, when the degradation activity donor 110 has the a few-layer structure, the degradation activity donor 110 has an odd number of layers. As such, a more significant piezoelectric property can be provided. Preferably, a number of layers of the few-layer structure is less than or equal to 9, but the present disclosure is not limited thereto. The degradation activity donor 110 can be in a form of powders and shown in FIG. 1, and a particle size of each of the powders ranges from 1 nm to 1000 μm. The term "powder" can be but is not limited to a nanoflower.

The supporter 120 is applied to carry the degradation activity donor 110, and completely or partially cover the degradation activity donor 110. Accordingly, any substance which can achieve the aforementioned functionalities can be the supporter 120 of the present disclosure. A Young's modulus of the supporter 120 can range from 100 Pa to 300 GPa. Therefore, the elasticity of the supporter 120 is sufficient, which can prevent the supporter 120 from being broken by the external force. The supporter 120 can be asphalt or a polymer. The polymer can be a thermoplastic polymer or a thermosetting polymer. Specifically, the polymer can be but is not limited to poly(methyl methacrylate) (PMMA), polymerized siloxane, polyethylene terephthalate (PET), poly(ethylene naphthalate) (PEN), polytetrafluoroethylene (PTFE), polyimide or polyvinylidene difluoride (PVDF). A specific example of the polymerized siloxane can be but is not limited a cured polydimethylsiloxane (PDMS). The polymer can be manufactured by a free radical polymerization of unsaturated monomers. Alternatively, the polymer can be manufactured by a cross-linking reaction. Alternatively, the polymer can be manufactured by a condensation reaction of monomers with functional groups. For example, PET can be manufactured by a condensation reaction of dimethyl terephthalate dimethyl and ethylene glycol. PEN can be manufactured by a condensation reaction of naphthalene-2,6-dicarboxylic acid and ethylene glycol. PTFE can be manufactured by a free radical polymerization of tetrafluoroethylene. Polyimide can be manufactured by a condensation reaction of dianhydride and diamine. PVDF can be manufactured by a free radical polymerization of vinylidene difluoride. That is, reactants of the polymerization to manufacture the polymer, such as monomers and additives, can be adjusted according to the kind of the polymer. The additive can be but is not limited a catalyst, a curing agent (a hardening agent) or a free radical initiator.

The composite structure 100 can be porous. For example, the supporter 120 can be a porous supporter. Alternatively, the composite structure 100 can be drilled so as to from a plurality holes.

Figure 2A:
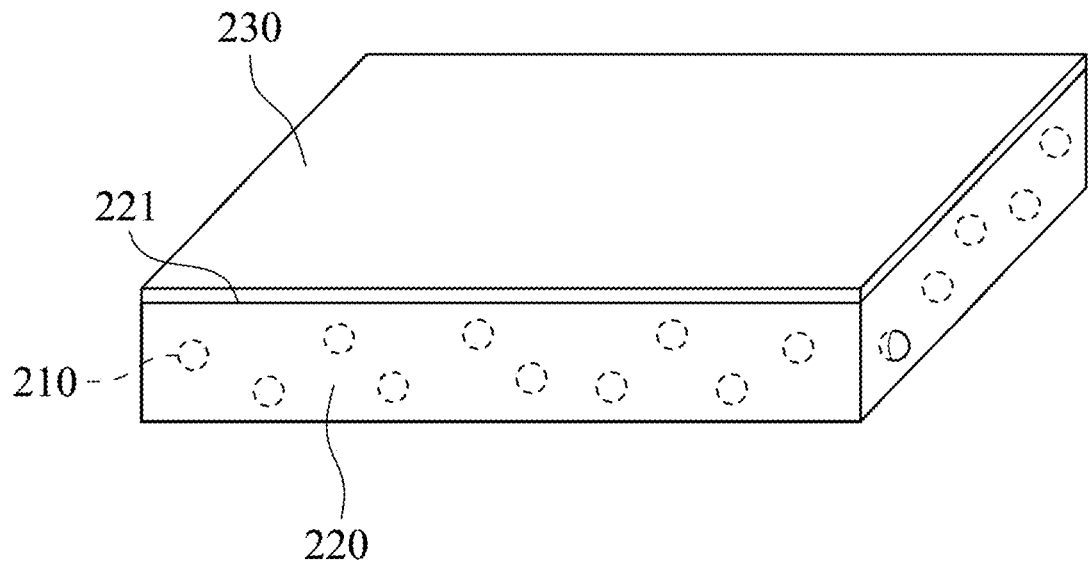
FIG. 2A is a 3D view of a composite structure according to the 2nd embodiment of the present disclosure.

FIG. 2A is a 3D view of a composite structure 200 according to the 2nd embodiment of the present disclosure. In FIG. 2A, the composite structure 200 includes a degradation activity donor 210, a supporter 220 and a conductive part 230. The conductive part 230 is disposed on a surface 221 of the supporter 220. Therefore, the degradation activity of the composite structure 200 can be enhanced. The degradation activity donor 210 can be the same as the degradation activity donor 110 in FIG. 1, and the supporter 220 can be the same as the supporter 120 in FIG. 1. Therefore, details of the degradation activity donor 210 and the supporter 220 are not repeated herein. The conductive part 230 can be made of a conductive material. The conductive material refers to a material which can assist the transportation of electrons and holes. The conductive material can be but is not limited to metal, conductive polymer, indium tin oxide (ITO) or F-doped tin oxide (FTO). The metal can be but is not limited to gold, silver, copper or a combination thereof. In other embodiments, the conductive part can be disposed on two opposite surfaces of the supporter (not shown) or can be disposed on all surfaces of the supporter so as to completely cover the composite structure (not shown).

Figure 2B:
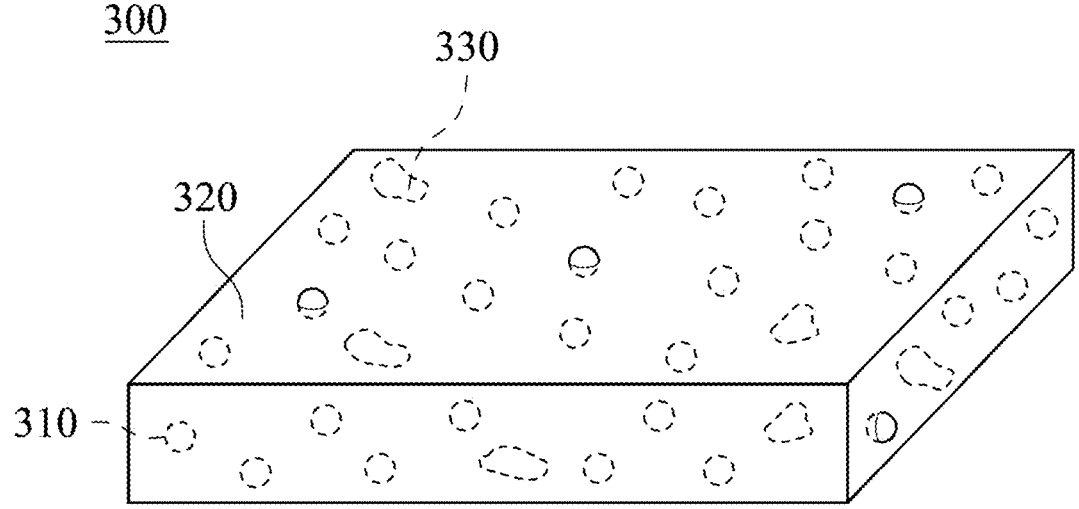
FIG. 2B is a 3D view of a composite structure according to the 3rd embodiment of the present disclosure.

FIG. 2B is a 3D view of a composite structure 300 according to the 3rd embodiment of the present disclosure. In FIG. 2B, the composite structure 300 includes a degradation activity donor 310, a supporter 320 and a conductive part 330. The conductive part 330 is embedded in the supporter 320. Therefore, the degradation activity of the composite structure 300 can be enhanced. The degradation activity donor 310 can be the same as the degradation activity donor 110 in FIG. 1, the supporter 320 can be the same as the supporter 120 in FIG. 1, and the conductive part 330 can be the same as the conductive part 230 in FIG. 2A. Therefore, details of the degradation activity donor 310, the supporter 320 and the conductive part 330 are not repeated herein.

Figure 3A:
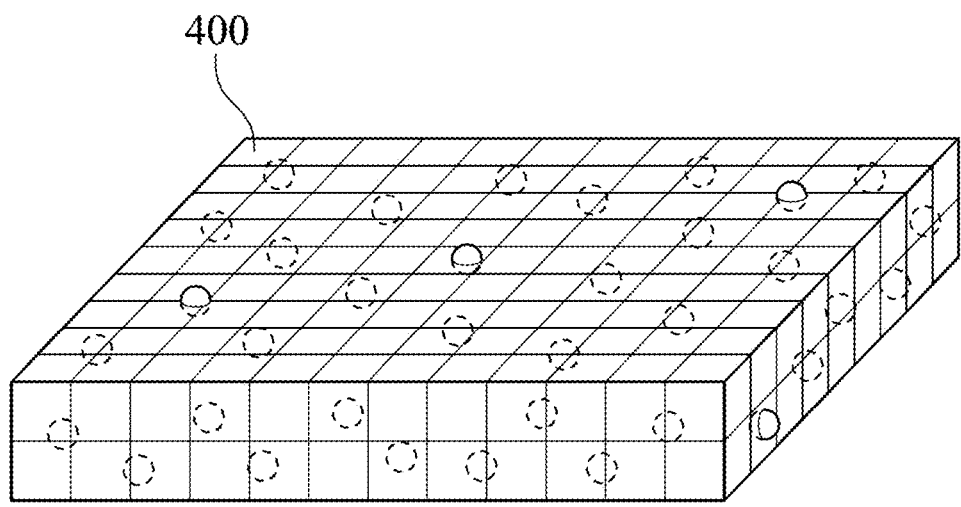
FIG. 3A is a 3D view of composite structures according to the 4th embodiment of the present disclosure.

FIG. 3A is a 3D view of composite structures 400 according to the 4th embodiment of the present disclosure. A size of the composite structures 400 in FIG. 3A is smaller than a size of the composite structure 100 in FIG. 1. Specifically, the bulky composite structure 100 can be cut so as obtain the composite structures 400 in the form of particles. Therefore, the composite structures 400 can have an enhanced degradation activity comparing to the composite structure 100. A particle size of each of the composite structures 400 can range from 10 nm to 100 mm.

Figure 3B:
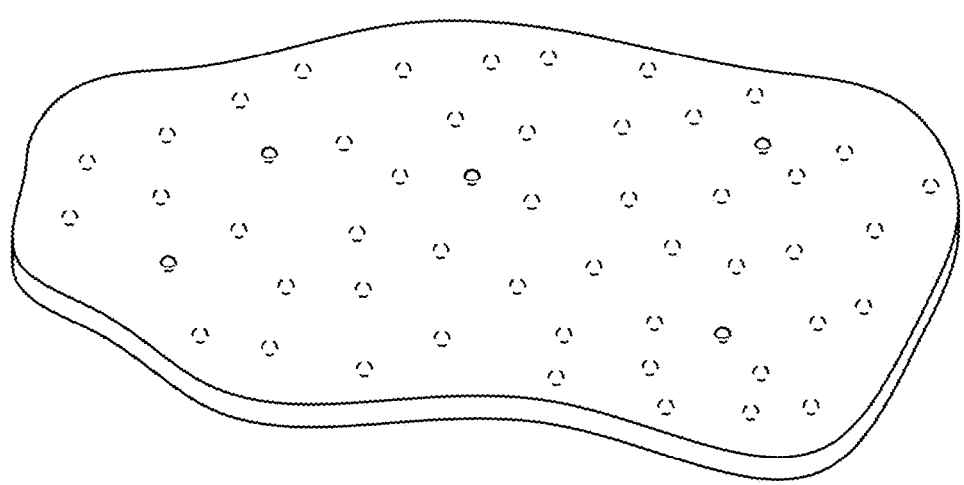
FIG. 3B is a 3D view of a composite structure according to the 5th embodiment of the present disclosure.

FIG. 3B is a 3D view of a composite structure 450 according to the 5th embodiment of the present disclosure. A thickness of the composite structure 450 in FIG. 3B is thinner than a thickness of the composite structure 100 in FIG. 1. Specifically, the composite structure 450 can be formed in a thin film, which is favorable for disposing the composite structure 450 on a wastewater treatment equipment or an air purification equipment. The thickness of the composite structure 450 can range from 10 nm to 100 mm.

Figure 4:
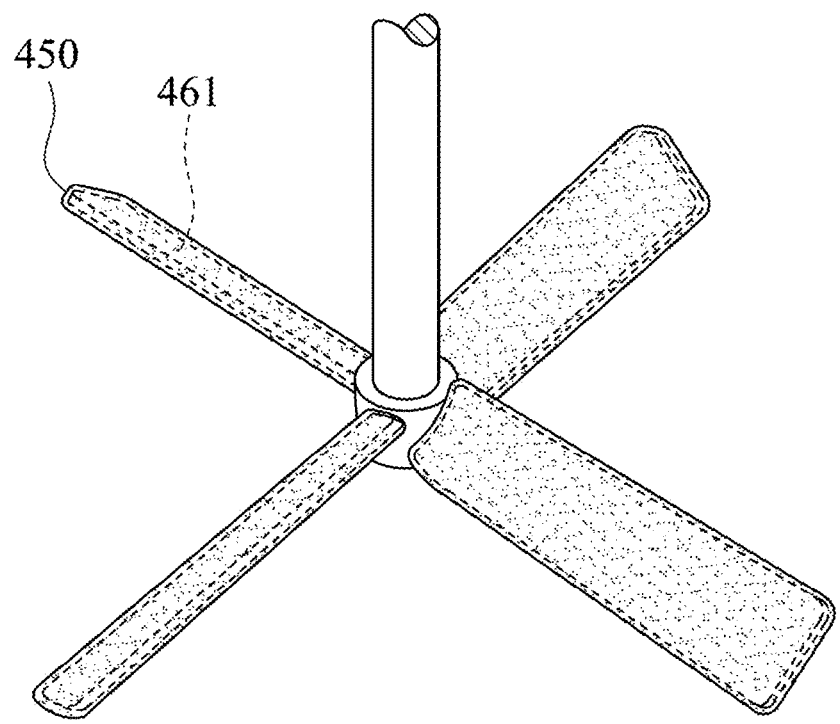
FIG. 4 is a schematic view showing a use state of the composite structure according to the 5th embodiment of the present disclosure.

FIG. 4 is a schematic view showing a use state of the composite structure 450 according to the 5th embodiment of the present disclosure. In FIG. 4, the composite structure 450 is disposed on blades 461 of a rotating component 460. The rotating component 460 can be a stirring component of the wastewater treatment equipment, or the rotating component 460 can be a fan of the air purification equipment. Therefore, when the rotating component 460 is rotated, the medium (wastewater or air) can be disturbed, whereby a mechanical stress which can cause a deformation of the composite structure 450 can be generated. Accordingly, the degradation activity of the composite structure 450 can be induced. In other embodiments, the composite structure can be formed in a thin film (composite structure 450) and be coated on a surface of a net structure (not shown), a wall (not shown) or a foaming structure (not shown). Alternatively, the composite structure can be formed in particles and be spread on the surface of the net structure, the wall or the foaming structure.

To sum up, the composite structure according to the present can be formed in a bulk (composite structure 100), in particles (composite structure 400) or in a thin film (composite structure 450). The maximum length of the composite structure can range from 1 nm to 100 m, and a thickness of the composite structure can range from 1 nm to 100 m.

Method for Manufacturing Composite Structure

Figure 5:
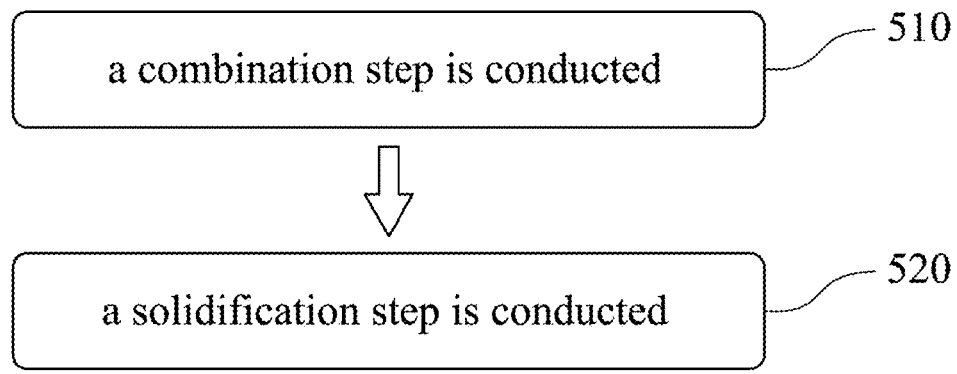
FIG. 5 is a flow diagram showing a method for manufacturing a composite structure according to the 6th embodiment of the present disclosure.

FIG. 5 is a flow diagram showing a method 500 for manufacturing a composite structure according to the 6th embodiment of the present disclosure. In FIG. 5, the method 500 for manufacturing the composite structure includes Step 510 and Step 520.

In Step 510, a combination step is conducted, in which a degradation activity donor is combined with a supporter precursor. The degradation activity donor has a piezoelectric property.

In Step 520, a solidification step is conducted, in which the supporter precursor is solidified to form a supporter so as to obtain the composite structure. In the composite structure, the supporter carries the degradation activity donor, and the degradation activity donor is completely or partially covered by the supporter.

The "supporter precursor" is a material to form the supporter, and the material can be transformed into the supporter after solidification. Take the asphalt as example, the supporter precursor can be an asphalt which is heated to be in a liquid state, which can be transformed into a solid state after cooling, and the asphalt in the solid state is the supporter. Take the polymer as example, when the supporter is the polymer, the supporter precursor can be a mixture of the reactants of the polymerization to manufacture the polymer. The reactants of the polymerization can include monomers and selectively include as least one additive and a solvent. The additive can include a free radical initiator, a catalyst and/or a curing agent. Alternatively, when the supporter is the polymer, the supporter precursor can be a varnish formed by the polymer and a solvent, which is favorable for forming the polymer in a thin film and is favorable for evenly distributing degradation activity donor in the polymer. For example, when the polymer is polyimide, the supporter precursor can be a polyimide/poly(amic acid) varnish which is formed by mixing the polyimide/poly (amic acid) and an organic solvent. When the polyimide/poly(amic acid) varnish is coated on a substrate and heated, the organic solvent can be removed and a ring-open reaction of the poly(amic acid) can be conducted so as to obtain a polyimide film. The polyimide film is the support. The foregoing supporter precursors are only exemplary, and the present disclosure is not limited thereto. A viscosity of the supporter precursor can range from 1 mPa·s to $1 \times 10^{25}$ Pa·s at 25° C.

The phrase "a degradation activity donor is combined with a supporter precursor" can refer that the degradation activity donor is mixed with the supporter precursor, or can refer that the degradation activity donor is disposed in or on the supporter precursor. According to one embodiment of the present disclosure, the degradation activity donor can be added into the supporter precursor, and the degradation activity donor and the supporter precursor can be mixed by stirring. As such, the majority of the degradation activity donor can be completely covered by the supporter. According to another embodiment of the present disclosure, when the supporter precursor in a semi-solidified state, the degradation activity donor can be blown to the supporter precursor by an air purge device with high pressure. As such, the majority of the degradation activity donor can be partially covered by the supporter.

The degradation activity donor can be the same as the degradation activity donor 110 in FIG. 1, the supporter can be the same as the supporter 120 in FIG. 1. Therefore, details of the degradation activity donor and the supporter are not repeated herein.

According to another embodiment of the present disclosure, when the combination step is conducted (i.e., Step 510), a conductive material is added, and the conductive material and the degradation activity donor are combined with the supporter precursor. Therefore, a conductive part can be formed by the conductive material, and the conductive part is embedded in the supporter (as shown in FIG. 2B). Details of the conductive part can be the same as that in FIG. 2A, and are not repeated herein.

Figure 6:
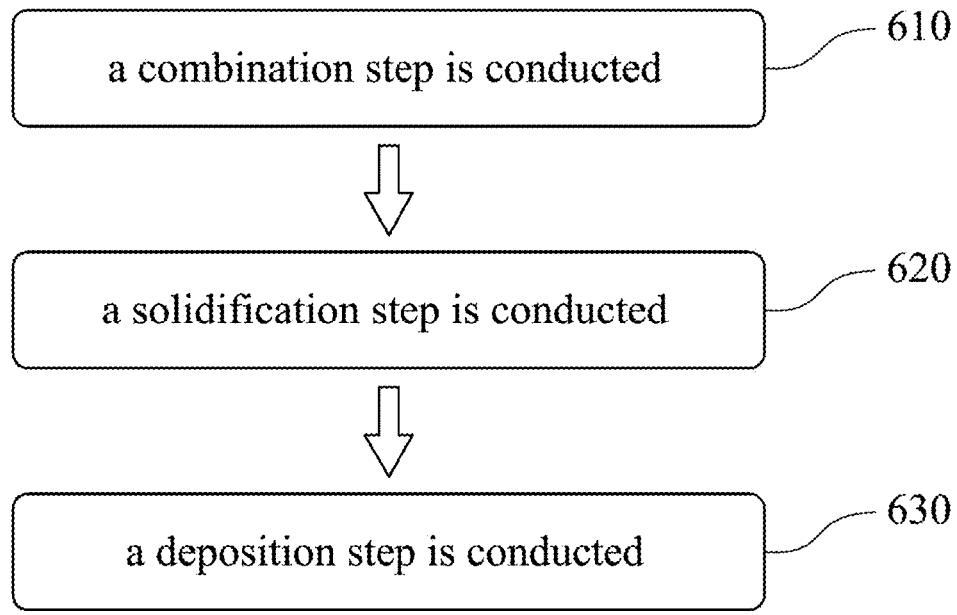
FIG. 6 is a flow diagram showing a method for manufacturing a composite structure according to the 7th embodiment of the present disclosure.

FIG. 6 is a flow diagram showing a method 600 for manufacturing a composite structure according to the 7th embodiment of the present disclosure. In FIG. 6, the method 600 for manufacturing the composite structure includes Step 610, Step 620 and Step 630.

In Step 610, a combination step is conducted. In Step 620, a solidification step is conducted. Details of Step 610 and Step 620 can be the same as Step 510 and Step 520 in FIG. 5, and are not repeated herein.

In Step 630, a deposition step is conducted, wherein a conductive part is disposed on a surface of the supporter (as shown in FIG. 2A). The conductive part can be the same as that in FIG. 2A, and are not repeated herein. Specifically, the deposition step can be implemented by a coating technique. The coating technique can be but is not limited to vacuum sputtering deposition.

Method for Degrading Organic Material

Figure 7:
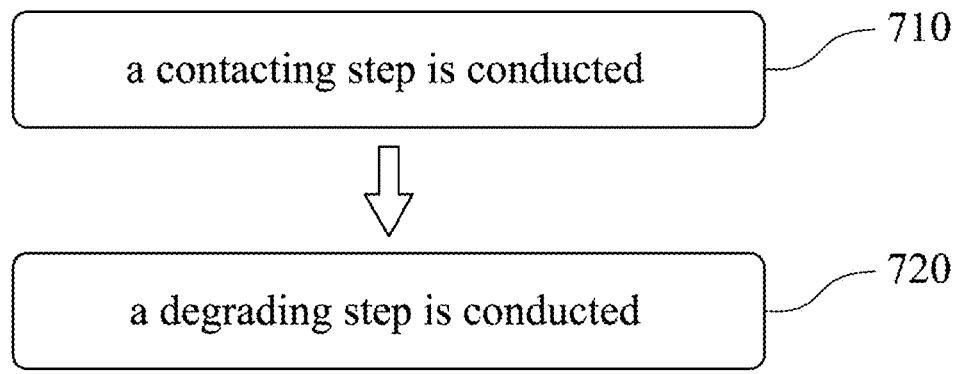
FIG. 7 is a flow diagram showing a method for degrading an organic material according to the 8th embodiment of the present disclosure.

FIG. 7 is a flow diagram showing a method 700 for degrading an organic material according to the 8th embodiment of the present disclosure. In FIG. 7, the method 700 for degrading the organic material includes Step 710 and Step 720.

In Step 710, a contacting step is conducted, in which the composite structure according to the present disclosure is contacted with a medium. The medium includes at least one organic material and water. The medium can be an aqueous solution or an air.

In Step 720, a degrading step is conducted, in which a mechanical perturbation is generated in the medium to polarize the degradation activity donor, and a separation of an electron-hole pair is generated for degrading the organic material.

Specifically, when the mechanical perturbation is generated in the medium, the mechanical stress which can cause the deformation of the degradation activity donor can be provided, and the polarization of the degradation activity donor can be induced so as to generate a separation of electron-hole pairs. The electrons and the holes can be reacted with other molecules (such as water molecules) in the medium so as to generate reactive free radicals. Accordingly, the organic material can be degraded by redox reactions. In other words, the composite structure according to the present disclosure can be applied to degrade the organic materials in wastewater. In the application example, the medium is the aqueous solution formed from the wastewater. The composite structure can be added into the treatment channel of the wastewater. Alternatively, the composite structure can be coated on the components of the wastewater treatment equipment (such as on the surface of a stirring component or an inner wall of a waterpipe). The wastewater flows due to different water pressures (the flow of the wastewater includes partially vortexes and disturbances). The flow of the wastewater can be regarded as the mechanical perturbation, which can cause the polarization of the degradation activity donor of the composite structure and cause following redox reactions. Accordingly, the organic materials in the wastewater can be degraded so as to achieve a water purification effect. Alternatively, the composite structure according to the present disclosure can be applied to degrade organic gases in air. For example, the composite structure according to the present disclosure can be formed in particles and be sprinkled on a filter of an air purifier. In the application example, the medium is the air. The air includes water vapor. When the air flows due to the different air pressures (the flow of air includes partial vortexes and disturbances) and goes through the filter sprinkled with the composite structure, the flow of the air can be regarded as the mechanical perturbation, which can cause the polarization of the degradation activity donor of the composite structure. An inner electric field and the separation of the electron-hole pairs are generated, which cause the following redox reactions. Accordingly, the organic gases in the air can be degraded so as to achieve a deodorization effect and an air purification effect. Moreover, using the supporter to completely or partially cover the degradation activity donor violates the teaching in the art. According to the ordinary knowledge in the art, when the degradation activity donor is covered by the supporter, the contact between the electrons/holes and other molecules will be blocked, which is unfavorable for forming the reactive free radicals and unfavorable for providing an effective degradation activity. Therefore, there are no examples in which the degradation activity donor is completely or partially covered by the supporter prior to the present disclosure. In the present disclosure, with the composite structure in which the degradation activity donor is completely or partially covered by the supporter, the difficulty of recovering the degradation activity donor by centrifugal method due to an excessive light weight thereof can be eased, the problem of the second pollution can be prevented. Moreover, the degradation activity donor can be protected by the supporter, the damage degree of the degradation activity donor caused by the external force can be reduced, which is favorable for repeated use. Furthermore, the composite structure can provide the desired degradation activity, which can be attributed to that the electron can migrate to the surface of the composite structure by hopping, so that the electron can still react with other molecules so as to provide the desired degradation activity.

More specifically, the medium can be but is not limited to a wastewater of a factory. For example, the medium can be a volatile organic wastewater of a semiconductor factory, a wastewater containing dyes of a dyeing and finishing factory, or a wastewater containing electroplate liquid of an electroplate factory. The organic material can be but is not limited to a volatile organic material, an organic acid, an organic base, an ammonia nitrogen or a dye. Moreover, the total organic carbon (TOC) in the medium can be effectively reduced by the method 700 for degrading an organic material according to the present disclosure.

Method for Sterilizing

Figure 8:
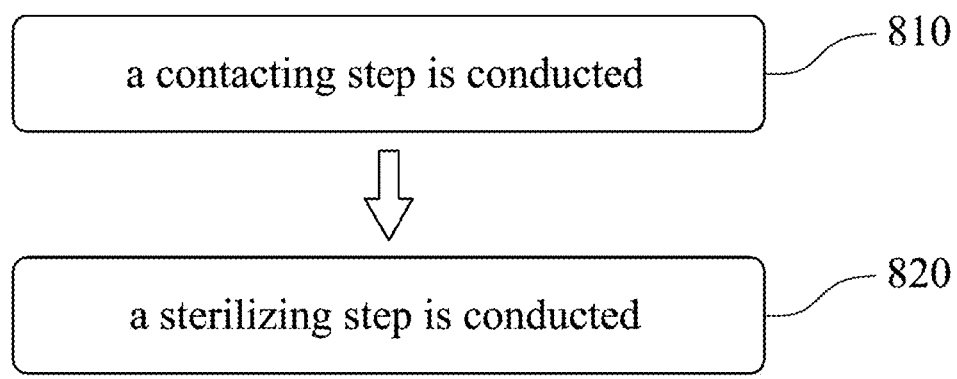
FIG. 8 is a flow diagram showing a method for sterilizing according to the 9th embodiment of the present disclosure.

FIG. 8 is a flow diagram showing a method 800 for sterilizing according to the 9th embodiment of the present disclosure. In FIG. 8, the method 800 for sterilizing includes Step 810 and Step 820.

In Step 810, a contacting step is conducted, in which the composite structure according to the present disclosure is contacted with a medium, and the medium includes at least one bacterium and water.

In Step 820, a sterilizing step is conducted, in which a mechanical perturbation is generated in the medium to polarize the degradation activity donor, and a separation of an electron-hole pair is generated for killing the bacterium. The medium can be an air or an aqueous solution. That is, the composite structure according to the present disclosure can be applied to kill the bacteria in aqueous solution or in air. The bacteria can be but is not limited to mildew, Escherichia coli, Pseudomonas aeruginosa, Staphylococcus, Pyogenic bacteria and Trichophyton. Specifically, when the mechanical perturbation is generated in the medium, the mechanical stress which can cause the deformation of the degradation activity donor can be provided, and the polarization of the degradation activity donor can be induced so as to generate a separation of electron-hole pairs. The electrons and the holes can be reacted with other molecules (such as water molecules) in the medium so as to generate reactive free radicals. Accordingly, the bacteria can be killed by redox reactions so as to achieve the sterilizing effect. More specifically, the composite structure according to the present disclosure can be coated on a filter. The filter can be disposed in the channels of the aqueous solution (wastewater or tap water). Therefore, when the aqueous solution runs through the filter, the sterilizing effect can be achieved. The principles of the method for sterilizing and the method for degrading an organic material according to the present disclosure are the same, except the two methods are applied to different objects, the former is applied to bacteria and the latter is applied to organic materials. Therefore, other details of the method for sterilizing can be referred to the description of FIG. 7, and are not repeated herein.

Synthesis Examples and Property Thereof

Synthesis Example 1: the degradation activity donor $MoS_2$ powders are synthesized by a hydrothermal method. First, 0.72 g sodium molybdenum oxide dihydrate ($Na_2MoO_4·2H_2O$) and 0.69 g thiourea ($CH_4N_2S$) are put into a beaker, then are dissolved in a solution of 1-butyl-3-methylimidazolium chloride ([BMIM][Cl], 1 M, 1 ml) to obtain a precursor A1. 1 ml hydrochloric acid (HCl, 12 M) is diluted in deionized water to form a 60 ml acid solution. The acid solution is slowly titrated into the beaker containing the precursor A1 in 30 minutes, then is stirred for 12 hours to obtain a solution B1. Afterwards, the solution B1 is put into a hydrothermal container made of teflon and then put into an oven maintained at a temperature of 220° C. for 24 hours. Let the hydrothermal container stand still until the temperature thereof is reduced to the room temperature. The suspension in the hydrothermal container is centrifuged for collecting a precipitation. Then the precipitation is washed with deionized water and then collected by centrifugation, which is repeated four times. Then the precipitation is washed with ethanol and then collected by centrifugation. The precipitation is put into the oven and is heated at 50° C. for 12 hours. Thus, the $MoS_2$ powders of Synthesis Example 1 are obtained. The $MoS_2$ powders are in the form of nanoflowers, and are named as $MoS_2$ NFs.

Figure 9A:
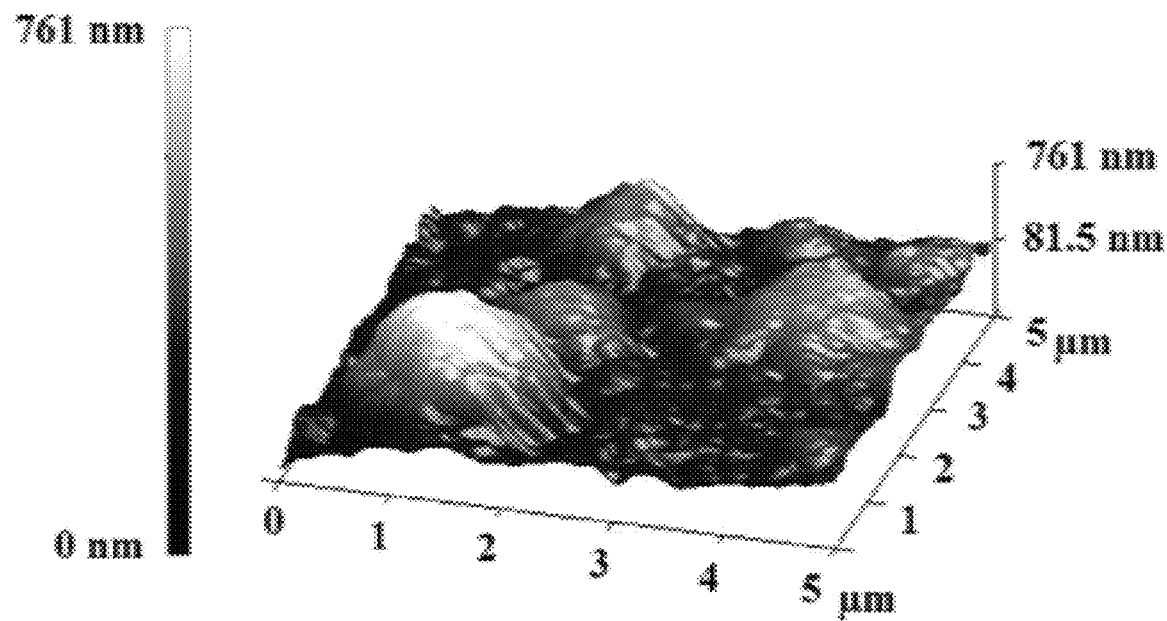
FIG. 9A shows a surface morphology of Synthesis Example 1.
Figure 9B:
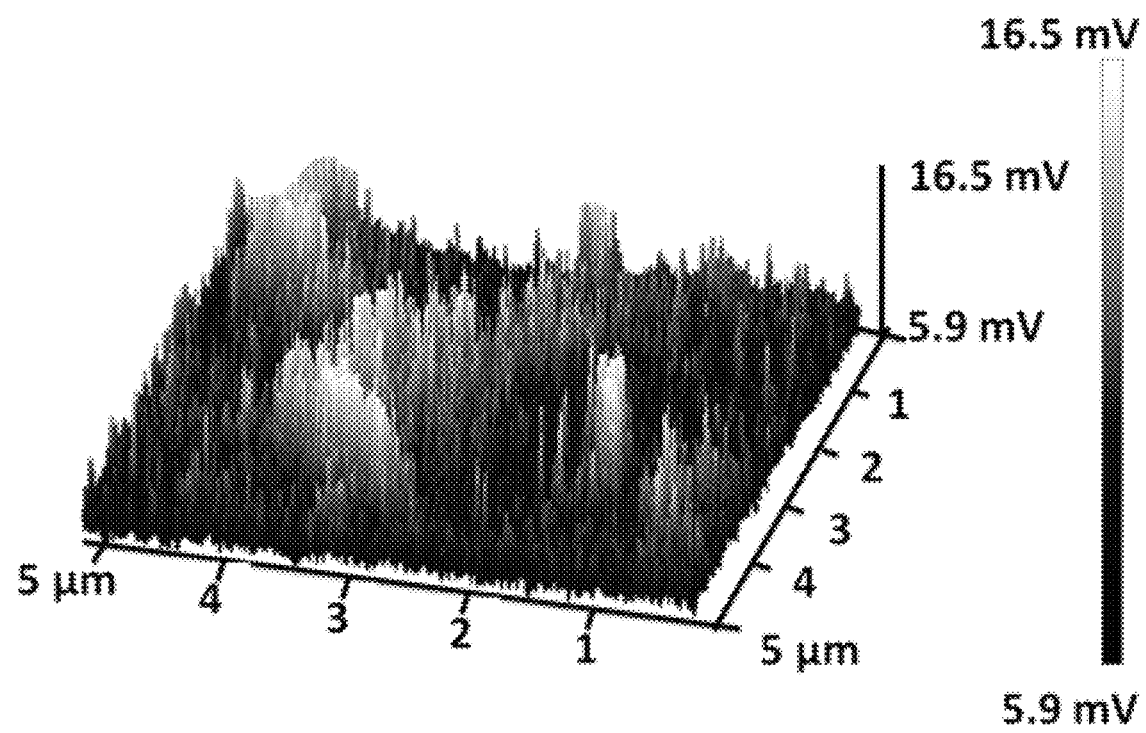
FIG. 9B is a 3D view showing the voltage potential distribution of FIG. 9A.

The piezoelectric property of the $MoS_2$ powders of Synthesis Example 1 is observed by a scanning probe microscope system (SPMs, Bruker Dimension ICON), and the results are shown in FIG. 9A and FIG. 9B. FIG. 9A shows a surface morphology of Synthesis Example 1. FIG. 9B is a 3D view showing the voltage potential distribution of FIG. 9A. As shown in FIG. 9A and FIG. 9B, the $MoS_2$ powders of Synthesis Example 1 have the piezoelectric property.

Synthesis Example 2: the degradation activity donor $WS_2$ powders are synthesized by a hydrothermal method. First, 5 mmol sodium tungstate dihydrate ($Na_2WO_4·2H_2O$) and 25 mmol thiourea ($CH_4N_2S$) are put into a beaker, then are dissolved in 50 ml deionized water. A [BMIM][Cl] solution (0.0028 M, 1 ml) is added into the beaker to obtain a precursor A2. 1 ml HCl (12 M) is diluted in deionized water to form a 60 ml acid solution. The acid solution is slowly titrated into the beaker containing the precursor A2 in 30 minutes, then is stirred at 25° C. for 1 hour to obtain a solution B2. Afterwards, the solution B2 is put into a hydrothermal container made of teflon and then put into an oven maintained at a temperature of 220° C. for 48 hours. Let the hydrothermal container stand still until the temperature thereof is reduced to the room temperature. The suspension in the hydrothermal container is centrifuged for collecting a precipitation. Then the precipitation is washed with deionized water and then collected by centrifugation, which is repeated four times. Then the precipitation is washed with ethanol and then collected by centrifugation. The precipitation is put into the oven and is heated at 40° C. for 12 hours. Thus, the $WS_2$ powders of Synthesis Example 2 are obtained. The $WS_2$ powders are in the form of nanoflowers, and are named as $WS_2$ NFs.

Figure 10A:
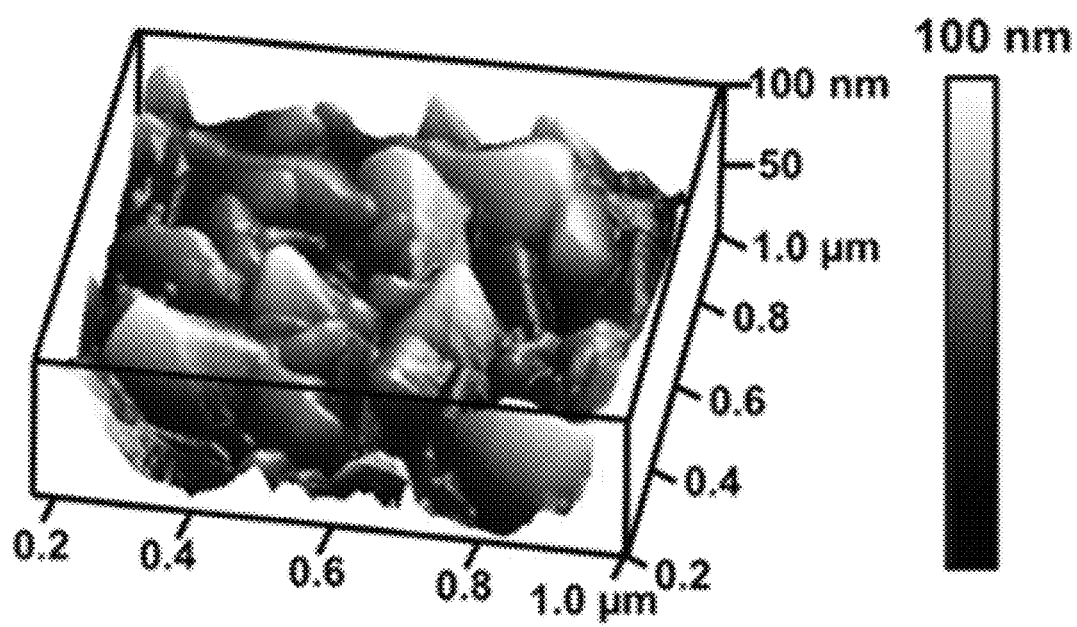
FIG. 10A shows a surface morphology of Synthesis Example 2.
Figure 10B:
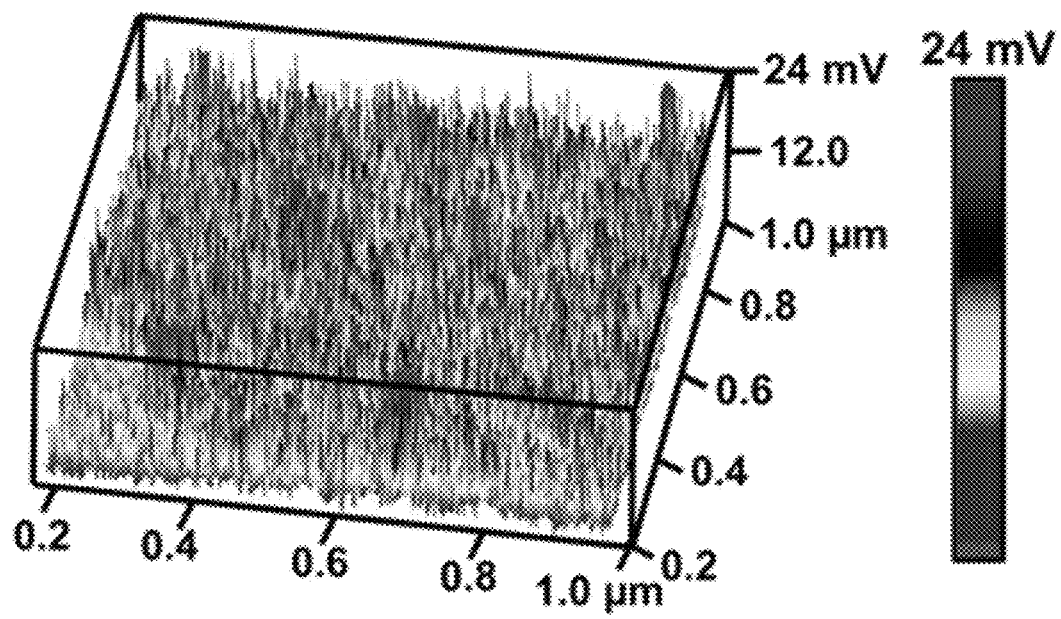
FIG. 10B is a 3D view showing the voltage potential distribution of FIG. 10A.

The piezoelectric property of the $WS_2$ powders of Synthesis Example 2 is observed by the SPMs, and the results are shown in FIG. 10A and FIG. 10B. FIG. 10A shows a surface morphology of Synthesis Example 2. FIG. 10B is a 3D view showing the voltage potential distribution of FIG. 10A. As shown in FIG. 10A and FIG. 10B, the $WS_2$ powders of Synthesis Example 2 have the piezoelectric property.

Synthesis Example 3: the degradation activity donor $WTe_2$ powders are synthesized by a Schlenk line technique. First, 3.5 mmol diphenyl ditelluride powders (DPDT, $C_{12}H_{10}Te_2$) are put into a 20 ml scintillation vial containing 10 ml oleylamine (OLA, $C_{18}H_{35}NH_2$), then DPDT and OLA are well dispersed under ultrasonic vibration for 15 minutes so as to obtain a OLA-DPDT solution. Afterwards, 3.5 mmol tungsten hexacarbonyl ($W(CO)_6$) powders are added into a 50 ml three-necked flask containing 40 ml OLA and the mixture is degassed under vacuum at 120° C. for 10 minutes. Next, the three-necked flask is purged with Ar gas and heated to 300° C. using a heating ramp of 12° C. $min^{-1}$. Then, the OLA-DPDT solution is continuously injected into the three-necked flask at 0.2 ml $min^{-1}$ using a syringe pump. After that, the temperature is increased to 320° C. and maintained at 320° C. for 24 hours. The three-necked flask is cooled to room temperature, the $WTe_2$ powders are precipitated by adding 50 ml of toluene and 25 ml of butanol and then collected by centrifugation. Then the precipitation is washed with a mixture of toluene and butanol with a volume ratio of 2:1 and then collected by centrifugation, which is repeated four times. The precipitation then is suspended in ethanol to form a dark black colloidal suspension for further characterization. The $WTe_2$ powders can be obtained by evaporating the ethanol. The $WTe_2$ powders of Synthesis Example 3 are in the form of nanoflowers, and are named as $WTeS_2$ NFs.

Figure 11A:
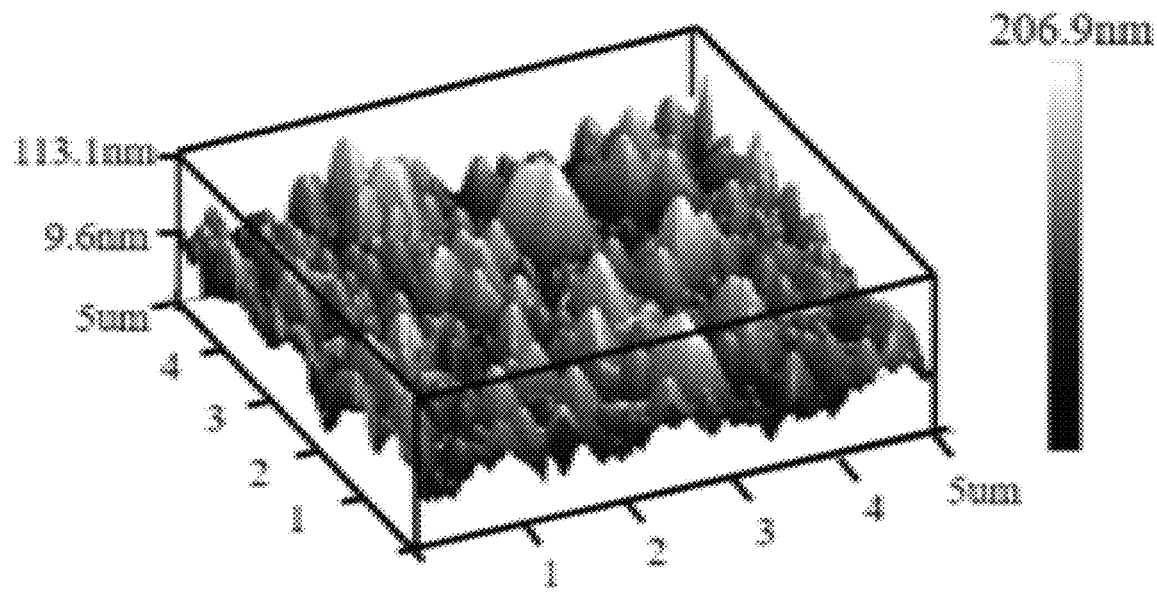
FIG. 11A shows a surface morphology of Synthesis Example 3.
Figure 11B:
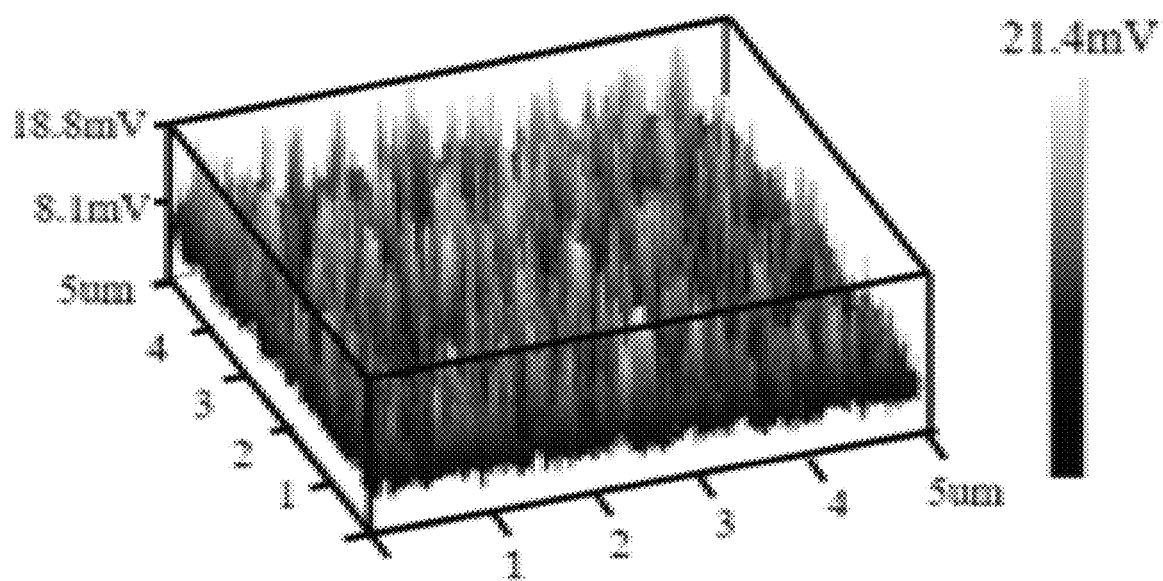
FIG. 11B is a 3D view showing the voltage potential distribution of FIG. 11A.

The piezoelectric property of the $WTe_2$ powders of Synthesis Example 3 is observed by the SPMs, and the results are shown in FIG. 11A and FIG. 11B. FIG. 11A shows a surface morphology of Synthesis Example 3. FIG. 11B is a 3D view showing the voltage potential distribution of FIG. 11A. As shown in FIG. 11A and FIG. 11B, the $WTe_2$ powders of Synthesis Example 3 have the piezoelectric property.

Synthesis Example 4: the degradation activity donor $MoSe_2$ powders are synthesized by a hydrothermal method. First, 0.206 g sodium molybdenum oxide dihydrate ($Na_2MoO_4 \cdot 2H_2O$) and 0.222 g selenium (IV) oxide ($SeO_2$) are put into a beaker, then are dissolved in 58 ml deionized water. The hydrazine monohydrate $N_2H_4 \cdot HO_2$ is slowly added into the beaker to form a reactive solution. Afterwards, the reactive solution is put into a hydrothermal container made of teflon and then put into an oven maintained at a temperature of 220° C. for 24 hours. Let the hydrothermal container stand still until the temperature thereof is reduced to the room temperature, which takes about 4 hours to 5 hours. The suspension in the hydrothermal container is centrifuged for collecting a precipitation. Then the precipitation is washed with deionized water and ethanol and then collected by centrifugation. The precipitation is put into the oven and is heated at 70° C. for 24 hours. Thus, the $MoSe_2$ powders of Synthesis Example 4 are obtained. The $MoSe_2$ powders are in the form of nanoflowers, and are named as $MoSe_2$ NFs.

Figure 12A:
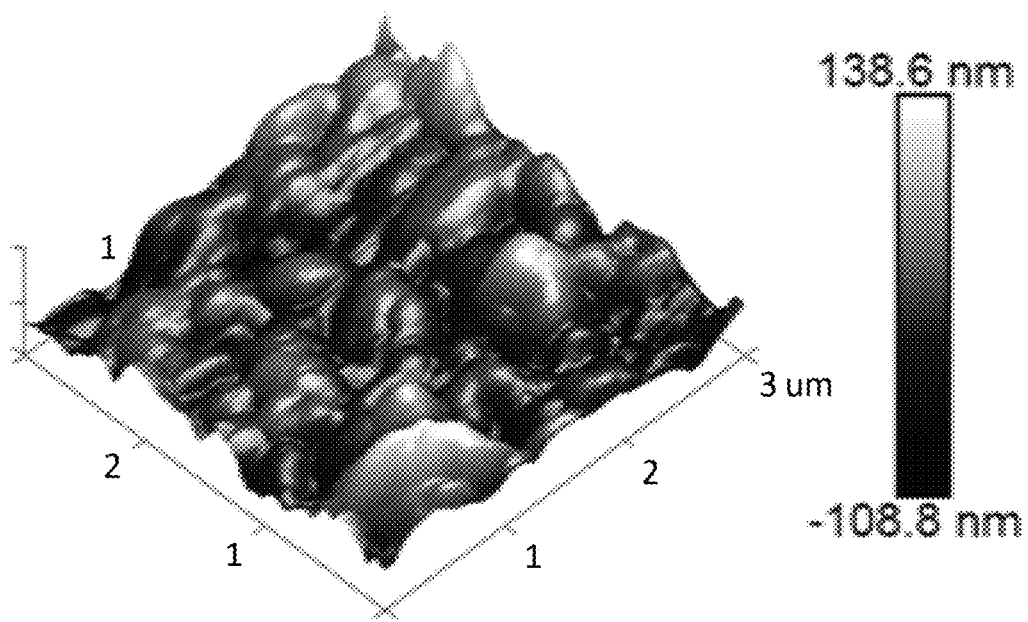
FIG. 12A shows a surface morphology of Synthesis Example 4.
Figure 12B:
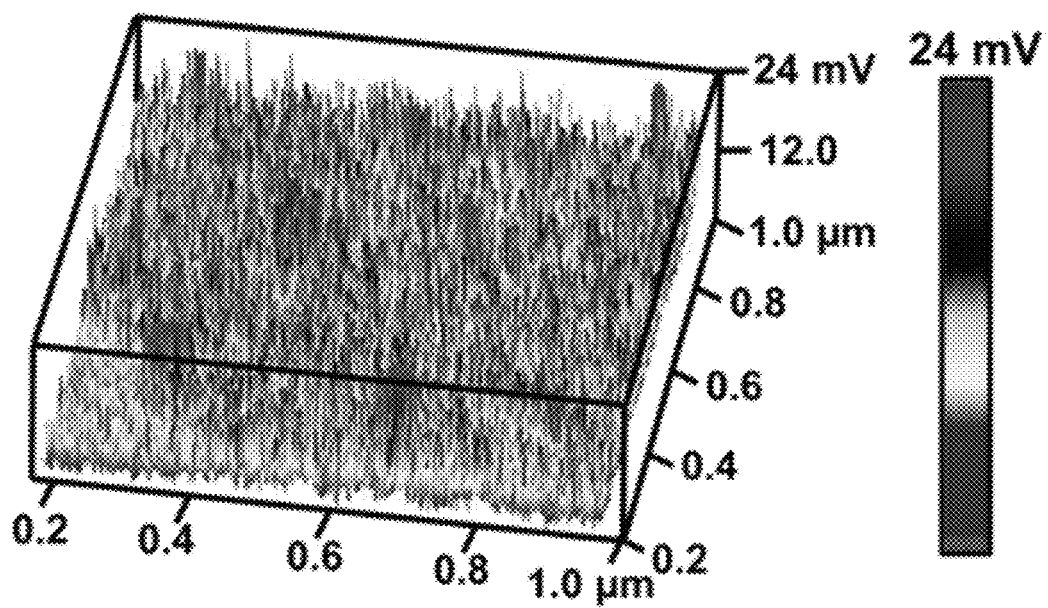
FIG. 12B is a 3D view showing the voltage potential distribution of FIG. 12A.

The piezoelectric property of the $MoSe_2$ powders of Synthesis Example 4 is observed by the SPMs, and the results are shown in FIG. 12A and FIG. 12B. FIG. 12A shows a surface morphology of Synthesis Example 4. FIG. 12B is a 3D view showing the voltage potential distribution of FIG. 12A. As shown in FIG. 12A and FIG. 12B, the $MoSe_2$ powders of Synthesis Example 4 have the piezoelectric property.

Examples and Property Thereof

Example 1 (EM 1): a composite structure $MoS_2$ NFs/PDMS is manufactured as follows. First, 10 g PDMS (part A of the product of SYLGARD® 184, which is purchased from DOW CORNING) and 5 g curing agent (part B of the product of SYLGARD® 184, which is purchased from DOW CORNING) are homogenously mixed so as to form a supporter precursor. Then 10 mg $MoS_2$ NFs powders of Synthesis Example 1 are added into the supporter precursor and are mixed with the supporter precursor to form a mixture. The mixture is heated at 100° C. for 1 hour, so that the supporter precursor in the mixture is solidified to form a support, i.e., the cured PDMS. Thus, the product of EM 1, the composite structure $MoS_2$ NFs/PDMS, is obtained. In EM1, most of the $MoS_2$ NFs are completely covered by the supporter, i.e., the cured PDMS.

Example 2 (EM 2): a composite structure $MoS_2$ NFs/PDMS is manufactured as follows. First, 10 g PDMS (part A of the product of SYLGARD® 184, which is purchased from DOW CORNING) and 5 g curing agent (part B of the product of SYLGARD® 184, which is purchased from DOW CORNING) are homogenously mixed so as to form a supporter precursor. The supporter precursor is heated at 60° C. for 0.5 hour, so that the supporter precursor is in a semi-solidified state. Then 10 mg $MoS_2$ NFs powders of Synthesis Example 1 are blown to the supporter precursor by an air purge device with high pressure, so that the $MoS_2$ NFs powders can be partially embedded in a surface of the supporter precursor which is in the semi-solidified state. Then the supporter precursor with the $MoS_2$ NFs powders is heated at 100° C. for 1 hour. The supporter precursor is solidified to form a support, i.e., the cured PDMS. Thus, the product of EM 2, the composite structure $MoS_2$ NFs/PDMS, is obtained. In EM2, most of the $MoS_2$ NFs are partially covered by the supporter, i.e., the cured PDMS.

Example 3 (EM 3): a composite structure $WS_2$ NFs/PDMS is manufactured as follows. The 10 mg $MoS_2$ NFs powders in EM 1 are replaced by 50 mg $WS_2$ NFs powders of Synthesis Example 2. Other steps and details of EM 3 are the same as that in EM 1, and are not repeated herein. Thus, the product of EM 3, the composite structure $WS_2$ NFs/PDMS, is obtained.

Example 4 (EM 4): a composite structure $MoSe_2$ NFs/PDMS is manufactured as follows. The 10 mg $MoS_2$ NFs powders in EM 1 are replaced by 10 mg $MoSe_2$ NFs powders of Synthesis Example 4. Other steps and details of EM 4 are the same as that in EM 1, and are not repeated herein. Thus, the product of EM 4, the composite structure $MoSe_2$ NFs/PDMS, is obtained.

Example 5 (EM 5): a composite structure $MoSe_2$ NFs/PDMS/Au is manufactured as follows. The composite structure of EM4 is further conducted with a deposition step. The deposition step is implemented by a vacuum sputtering system under the conditions of an Ar gas of 100 sccm, a gold target (99.9%) and a pressure of $1 \times 10^{-3}$ Torr. The deposition time is about 10 minutes. As such, the conductive part made of gold can be disposed on a surface of the supporter, i.e., the cured PDMS. Thus, the product of EM 5, the composite structure $MoSe_2$ NFs/PDMS/Au, is obtained.

Comparative Example 1 (Com EM 1): a cured PDMS is manufactured as follows. First, 10 g PDMS (part A of the product of SYLGARD® 184, which is purchased from DOW CORNING) and 5 g curing agent (part B of the product of SYLGARD® 184, which is purchased from DOW CORNING) are homogenously mixed so as to form a supporter precursor. The supporter precursor is heated at 100° C. for 1 hour. The supporter precursor is solidified to form a support, i.e., the cured PDMS. Thus, the product of Com EM 1, the cured PDMS, is obtained. The product of Com EM 1 only has the supporter and doesn't have the degradation activity donor.

Comparative Example 2 (Com EM 2): a composite structure $MoS_2$ sheet/PDMS is manufactured as follows. The 10 mg $MoS_2$ NFs powders in EM 1 are replaced by 10 mg $MoS_2$ which is commercial available (purchased from Sigma Aldrich Corporation). The commercial available MoS$_2$ is in the form of sheet, and doesn't have the piezoelectric property. Other steps and details of Com EM 2 are the same as that in EM 1, and are not repeated herein. Thus, the product of Com EM 2, the composite structure MoS$_2$ sheet/PDMS, is obtained.

Comparative Example 3 (Com EM 3): a composite structure TiO$_2$/PDMS is manufactured as follows. The 10 mg MoS$_2$ NFs powders in EM 1 are replaced by 10 mg TiO$_2$ which is commercial available (purchased from Sigma Aldrich Corporation). The commercial available TiO$_2$ is a conventional photocatalyst, and doesn't have the piezoelectric property. Other steps and details of Com EM 3 are the same as that in EM 1, and are not repeated herein. Thus, the product of Com EM 3, the composite structure TiO$_2$/PDMS, is obtained.

Comparative Example 4 (Com EM 4): a composite structure WS$_2$ bulk/PDMS is manufactured as follows. The 10 mg MoS$_2$ NFs powders in EM 1 are replaced by 10 mg WS$_2$ which is commercial available (purchased from Sigma Aldrich Corporation). The commercial available WS$_2$ is in the form of bulk, and doesn't have the piezoelectric property. Other steps and details of Com EM 4 are the same as that in EM 1, and are not repeated herein. Thus, the product of Com EM 4, the composite structure WS$_2$ bulk/PDMS, is obtained.

Comparative Example 5 (Com EM 5): a composite structure PDMS/Au is manufactured as follows. The composite structure of Com EM 5 is further conducted with a deposition step. The deposition step is implemented by the vacuum sputtering system under the conditions of an Ar gas of 100 sccm, a gold target (99.9%) and a pressure of $1\times10^{-3}$ Torr. The deposition time is about 10 minutes. As such, the conductive part made of gold can be disposed on a surface of the cured PDMS. Thus, the product of Com EM 5, the composite structure PDMS/Au, is obtained.

Comparative Example 6 (Com EM 6): a composite structure TiO$_2$/PDMS/Au is manufactured as follows. The composite structure TiO$_2$/PDMS of Com EM 3 is further conducted with a deposition step. The deposition step is implemented by the vacuum sputtering system under the conditions of an Ar of 100 sccm, a gold target (99.9%) and a pressure of $1\times10^{-3}$ Torr. The deposition time is about 10 minutes. As such, the conductive part made of gold can be disposed on a surface of the supporter, i.e., the cured PDMS. Thus, the product of Com EM 6, the composite structure TiO$_2$/PDMS/Au, is obtained.

Degradation Effect of Examples and Comparative Examples for Organic Material

Figure 13:
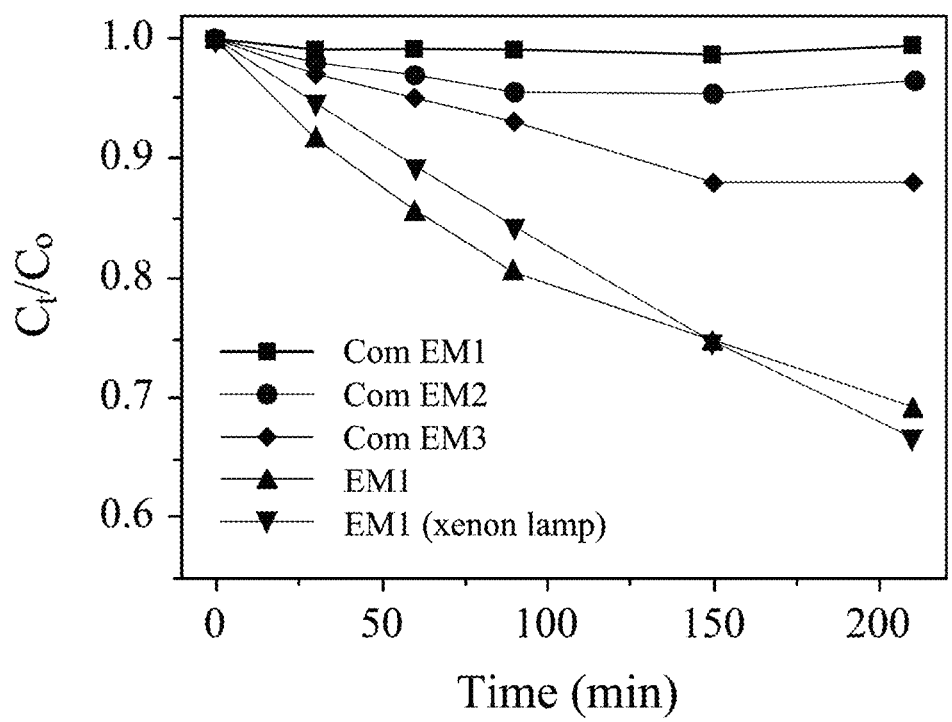
FIG. 13 shows degradation results of Example 1, Comparative Example 1, Comparative Example 2 and Comparative Example 3.

FIG. 13 shows degradation results of EM 1, Com EM 1, Com EM 2 and Com EM 3, in which $C_o$ represents an initial concentration of a Rhodamine-B (RB) solution, $C_t$ represents a concentration of the RB solution at the time point of t. When the concentration ratio $C_t/C_o$ is smaller, it indicates that the degradation effect is better. The concentration of the RB solution can be measured with a UV-vis spectrophotometer (Hitachi UV-3600, range of 250 nm to 800 nm). Hereinafter, the definitions of $C_o$ and $C_t$, and the measuring methods thereof are the same as that in FIG. 13, and are not repeated. FIG. 13 is obtained as follows. The products of EM 1 (15.01 g), Com EM 1 (15.00 g), Com EM 2 (15.01 g) and Com EM 3 (15.01 g) are put into a RB solution (40 ml, 10 ppm), respectively. The four RB solutions are put into a closed catalytic reaction container which can block lights, and applied with an ultrasonic wave of 40 kHz, 250 W. The concentrations of the four RB solutions are measured in a time interval of 1 minute to 30 minutes, which can be adjusted according to the degradation ratio. Moreover, the product of EM 1 (15.01 g) is put into a RB solution (40 ml, 10 ppm). The RB solution is applied with an ultrasonic wave of 40 kHz, 250 W and under the assistance of a xenon-lamp illumination. The concentration of the RB solution is measured in a time interval of 1 minute to 30 minutes, which can be adjusted according to the degradation ratio. The measured results are transformed into the concentration ratios $C_t/C_o$, and are plotted with time so as to obtain FIG. 13. As shown in FIG. 13, the composite structure according to the present disclosure can provide excellent degradation effect. Furthermore, the degradation effect of EM 1 is observed under the conditions of applying the ultrasonic wave in darkness and in the illumination of the xenon lamp, both of which can provide similar degradation effects. It shows that the composite structure according to the present disclosure can be induced by an external force (which is a kind of mechanical perturbation) and does not need to be irradiate with lights or rely on the irradiation of lights with short wavelength. Accordingly, it is favorable to reduce the energy consumption.

Figure 14A:
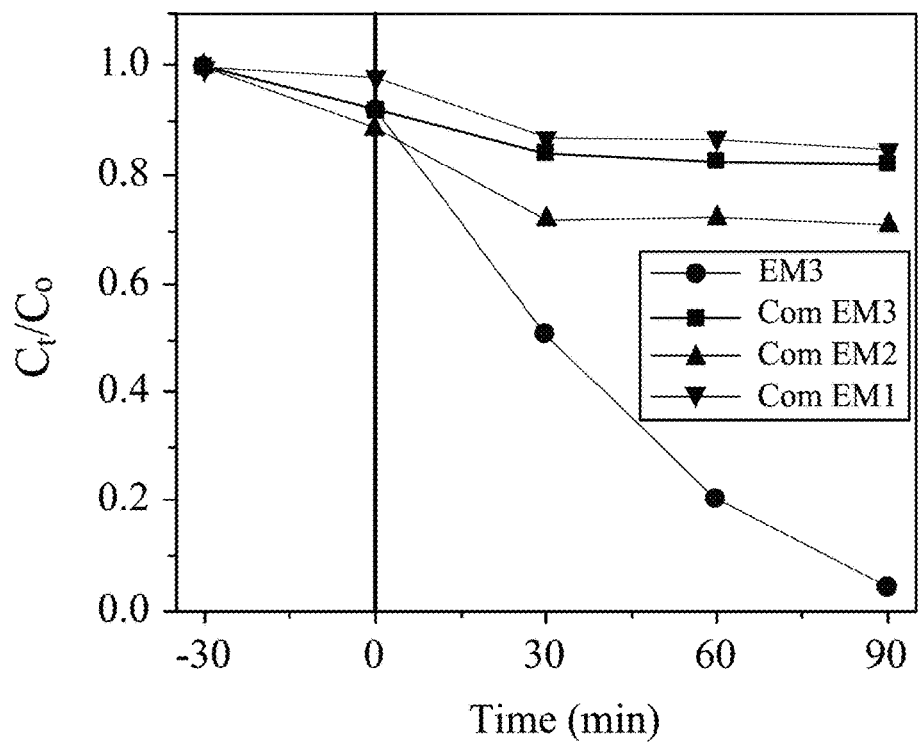
FIG. 14A shows degradation results of Example 3, Comparative Example 1, Comparative Example 2 and Comparative Example 3.

FIG. 14A shows degradation results of EM 3, Com EM 1, Com EM 2 and Com EM 3. FIG. 14A is obtained as follows. The products of EM 3 (15.05 g), Com EM 1 (15.00 g), Com EM 2 (15.01 g) and Com EM 3 (15.01 g) are put into a RB solution (40 ml, 10 ppm), respectively. The four RB solutions are put into a closed catalytic reaction container which can block lights. Let the RB solutions stand still for 30 minutes, then the concentrations of the four RB solutions are measured (which corresponding to the $C_t/C_o$ before the time point of zero in FIG. 14A). Afterwards, the four RB solutions in the closed catalytic reaction container are applied with an ultrasonic wave of 40 kHz, 250 W, the concentrations of the RB solutions are measured in a time interval of 30 minutes (which corresponding to the $C_t/C_o$ after the time point of zero in FIG. 14A). The measured results are transformed into the concentration ratios $C_t/C_o$, and are plotted with time so as to obtain FIG. 14A. As shown in FIG. 14A, before applying the ultrasonic wave, the concentrations of the four RB solutions only drop a little comparing to the initial concentrations thereof, and the degradation effect of EM 3 and Com EM 2 are similar. However, when the ultrasonic wave is introduced, the degradation ratio of EM 3 at 90 minutes is greater than 95%, which is far higher than that of Com EM 1, Com EM 2 and Com EM 3. It shows that the composite structure according to the present disclosure can be provide the piezo-catalyst effect.

Figure 14B:
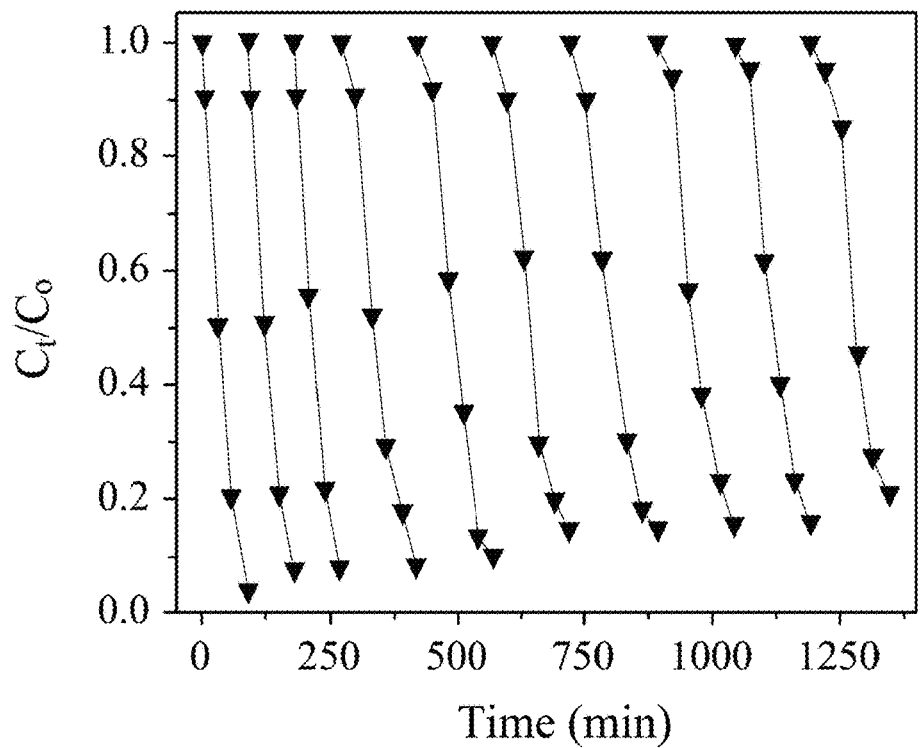
FIG. 14B shows cycling degradation results of Example 3.

FIG. 14B shows cycling degradation results of Example 3. FIG. 14B is obtained as follows. The product of EM 3 (15.05 g) is put into a RB solution (40 ml, 10 ppm). The RB solution is put into a closed catalytic reaction container which can block lights, and applied with an ultrasonic wave of 40 kHz, 250 W. The concentration of the RB solution is measured in a time interval of 5 to 10 minutes, which can be adjusted according to the degradation ratio. The aforementioned experiment is repeated 9 times. As shown in FIG. 14B, the degradation ratio of the composite structure of EM3 is greater than 95% at the first cycle, and is about 80% at the tenth cycle. It shows that the composite structure according to the present disclosure is favorable for repeated use.

Figure 15A:
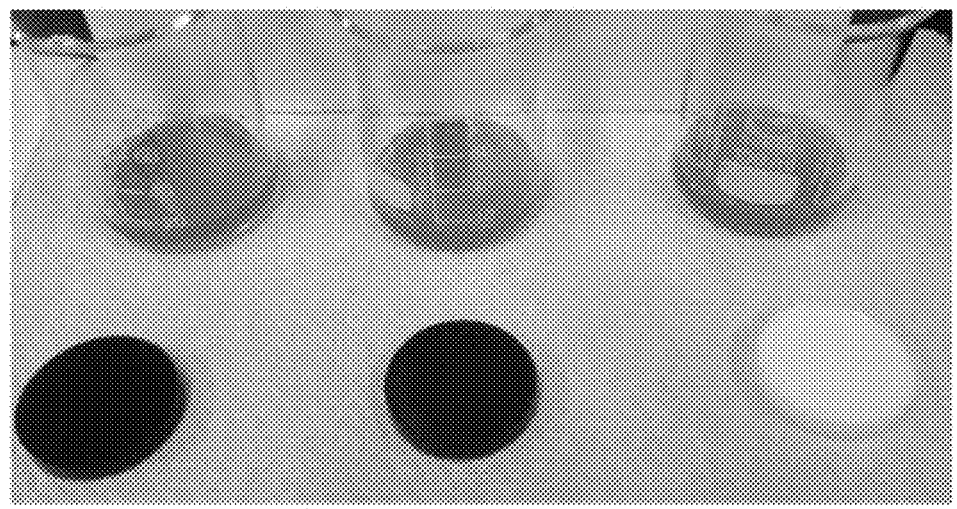
FIG. 15A shows appearances of Example 3, Comparative Example 4 and Comparative Example 3 before conducting a degradation experiment.
Figure 15B:
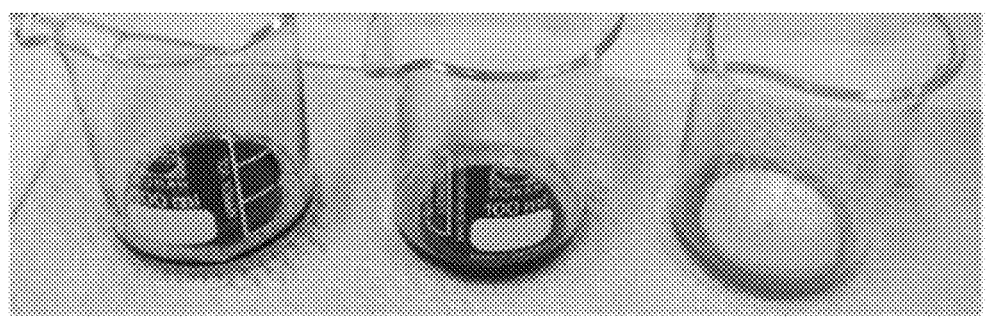
FIG. 15B shows appearances of Example 3, Comparative Example 4 and Comparative Example 3 after conducting the degradation experiment.

FIG. 15A shows appearances of EM 3, Com EM 4 and Com EM 3 before conducting a degradation experiment. FIG. 15B shows appearances of EM 3, Com EM 4 and Com EM 3 after conducting the degradation experiment. In FIG. 15A, there are three beakers, each of which contains 40 ml, 10 ppm RB solution. From left to right, the composite structures of EM 3, Com EM 4 and Com EM 3 are placed in front of the three beakers. The composite structures of EM 3, Com EM 4 and Com EM 3 are all formed in a bulk. The composite structures of EM 3, Com EM 4 and Com EM 3 are put into the three beakers, respectively. The three beakers are put into a closed catalytic reaction container which can block lights, and are applied with an ultrasonic wave of 40 kHz, 250 W for 90 minutes. As shown in FIG. 15B, the RB solution in the left beaker is almost transparent, and the color of the RB solution in the right beaker is darkest after the degradation experiment. It shows that the composite structure according to the present disclosure can provide an excellent degradation effect.

Figure 16:
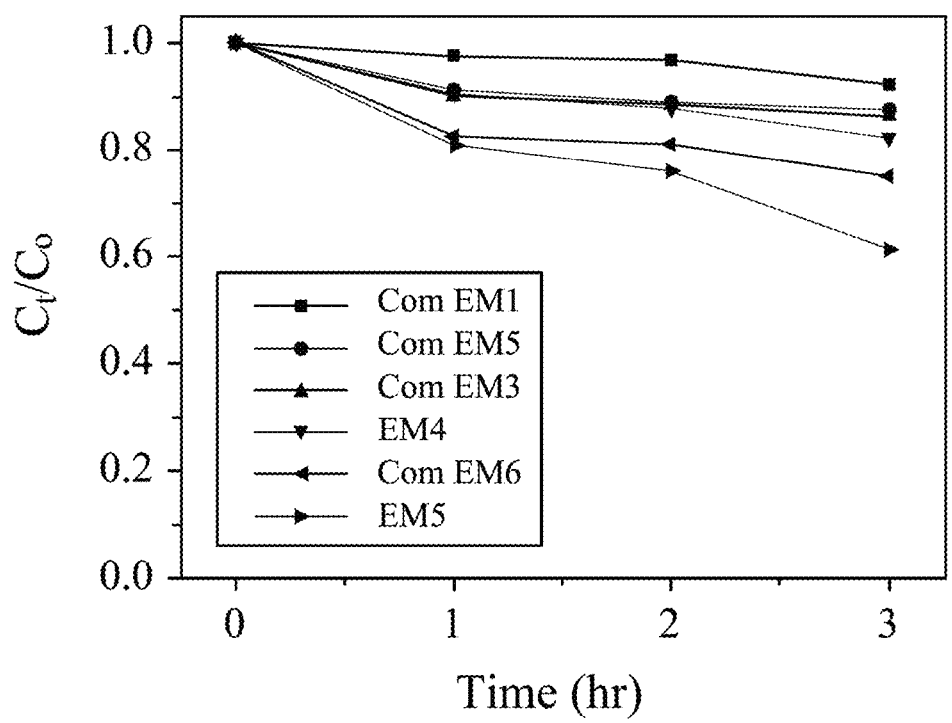
FIG. 16 shows degradation results of Example 4, Example 5, Comparative Example 1, Comparative Example 3, Comparative Example 5 and Comparative Example 6.

FIG. 16 shows degradation results of EM 4, EM 5, Com EM 1, Com EM 3, Com EM 5 and Com EM 6. As shown in FIG. 16, with the conductive part, the degradation effect can be enhanced.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A method for degrading an organism, comprising:
   providing a composite structure, wherein the composite structure comprises:
      a degradation activity donor having a piezoelectric property, wherein the degradation activity donor is a two-dimensional material with a non-centrosymmetric structure; and
      a supporter carrying the degradation activity donor, wherein the degradation activity donor is completely or partially covered by the supporter, and the supporter is made of a polymer or asphalt;
   conducting a contacting step, wherein the composite structure is contacted with a medium, and the medium comprises the organism and water; and
   conducting a degrading step, wherein a mechanical perturbation is generated in the medium to polarize the degradation activity donor, and a separation of an electron-hole pair is generated for degrading the organism.

2. The method for degrading an organism of claim 1, wherein the two-dimensional material with the non-centrosymmetric structure is molybdenum disulfide ($MoS_2$), tungsten ditelluride ($WTe_2$), molybdenum diselenide ($MoSe_2$), tungsten disulfide ($WS_2$) or a combination thereof.

3. The method for degrading an organism of claim 1, wherein the degradation activity donor is in a form of powders, and a particle size of each of the powders ranges from 1 nm to 1000 μm.

4. The method for degrading an organism of claim 1, wherein a Young's modulus of a material of the supporter ranges from 100 Pa to 300 GPa.

5. The method for degrading an organism of claim 1, wherein the supporter further comprises a conductive part, and the conductive part is disposed on a surface of the supporter or embedded in the supporter.

6. The method for degrading an organism of claim 1, wherein the organism is a bacterium.

7. The method for degrading an organism of claim 1, wherein the medium is an aqueous solution or an air.

8. The method for degrading an organism of claim 1, wherein the medium is a wastewater of a factory.

\* \* \* \* \*